(12) United States Patent
Bushman

(10) Patent No.: US 10,588,970 B2
(45) Date of Patent: *Mar. 17, 2020

(54) LOCALIZED IMMUNOSUPPRESSION OF ALLOGRAFTS FOR PERIPHERAL NERVE REPAIR

(71) Applicant: UNIVERSITY OF WYOMING, Laramie, WY (US)

(72) Inventor: Jared Bushman, Laramie, WY (US)

(73) Assignee: UNIVERSITY OF WYOMING, Laramie, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/035,362

(22) Filed: Jul. 13, 2018

(65) Prior Publication Data

US 2019/0008959 A1    Jan. 10, 2019

Related U.S. Application Data

(63) Continuation of application No. 15/457,359, filed on Mar. 13, 2017, now Pat. No. 10,064,938.

(60) Provisional application No. 62/307,290, filed on Mar. 11, 2016.

(51) Int. Cl.

| | |
|---|---|
| *A61K 39/395* | (2006.01) |
| *C07K 16/28* | (2006.01) |
| *A61K 38/13* | (2006.01) |
| *A61K 31/436* | (2006.01) |
| *A61K 31/573* | (2006.01) |
| *A61K 47/10* | (2017.01) |
| *A61K 9/51* | (2006.01) |
| *A61L 27/36* | (2006.01) |
| *A61L 27/48* | (2006.01) |
| *A61L 27/54* | (2006.01) |
| *A61K 45/06* | (2006.01) |
| *C07K 16/18* | (2006.01) |

(52) U.S. Cl.
CPC ........ *A61K 39/3955* (2013.01); *A61K 9/5153* (2013.01); *A61K 31/436* (2013.01); *A61K 31/573* (2013.01); *A61K 38/13* (2013.01); *A61K 39/39541* (2013.01); *A61K 45/06* (2013.01); *A61K 47/10* (2013.01); *A61L 27/3604* (2013.01); *A61L 27/3675* (2013.01); *A61L 27/48* (2013.01); *A61L 27/54* (2013.01); *C07K 16/18* (2013.01); *C07K 16/2809* (2013.01); *C07K 16/2866* (2013.01); *C07K 16/2893* (2013.01); *A61L 2430/32* (2013.01); *C07K 2317/24* (2013.01)

(58) Field of Classification Search
None
See application file for complete search history.

(56) References Cited

U.S. PATENT DOCUMENTS

| | | |
|---|---|---|
| 2003/0040112 A1 | 2/2003 | Muir |
| 2004/0063610 A1 | 4/2004 | Gold |
| 2005/0238625 A1 | 10/2005 | Chancellor et al. |
| 2010/0204683 A1 | 8/2010 | Bodor et al. |

OTHER PUBLICATIONS

Mekaj et al.: Application of topical pharmacological agents at the site of peripheral nerve injury and methods used for evaluating the success of the regenerative process. Journal of Orthopaedic Surgery and Research 2014 9:94.

McMurchy, Alicia N. et al., "Moving to tolerance: Clinical application of T regulatory cells",National Center for Biotechnology Information, Aug. 2011, <https://www.ncbi.nlm.nih.gov/pmc/articles/PMC3836227/>, last visited Jul. 15, 2019, Semin Immunol 23(4) , 23 pages.

Spence, Allyson et al., "Targeting Treg signaling for the treatment of autoimmune diseases", National Center for Biotechnology Information, Sep. 2015, <https://www.ncbi.nlm.nih.gov/pmc/articles/PMC4679451/>, last visited Jul. 15, 2019, Curr Opin Immunol 37:11-20.

Farini, Andrea et al., "Clinical Applications of Mesenchymal Stem Cells in Chronic Diseases", Hindawi Publishing Corporation, Apr. 2014, <https://www.hindawi.com/journals/sci/2014/306573/>, Jul. 15, 2019, Stem Cells International vol. 2014: Article ID 306573, 11 pages.

Zappia, Emanuel et al., "Mesenchymal stem cells ameliorate experimental autoimmune encephalomyelitis inducing T-cell anergy", American Society of Hematology, Apr. 2005, <http://www.bloodjournal.org/content/106/5/1755.short?sso-checked=true>, last visited Jul. 15, 2019, Blood 106 (5) :1755-1761.

Yolcu, Esma S. et al., "Pancreatic Islets Engineered with SA-FasL Protein Establish Robust Localized Tolerance by Inducing Regulatory T Cells in Mice", The Journal of Immunology, 19, <https://www.jimmunol.org/content/jimmunol/187/11/5901.full.pdf>, last visited Jul. 15, 2019, vol. 187:5901-5909, Nov. 2011.

Casiraghi, F. et al., "Localization of Mesenchymal Stromal Cells Dictates Their Immune or Proinflammatory Effects in Kidney Transplantation", American Journal of Transplantation, Apr. 2012, <https://onlinelibrary.wiley.com/doi/epdf/10.1111/j.1600-6143.2012.04115.x>, last visited on Jul. 15, 2019, vol. 12:2373-2383.

Jul, Hsiang-Yiang et al., "Autologous Mesenchymal Stem Cells Prevent Transplant Arteriosclerosis by Enhancing Local Expression of Interleukin-10, Interferon-?, and Indoleamine 2,3-dioxygenase", May 2012,<https://journals.sagepub.com/doi/full/10.3727/096368911X627525>, last visited on Jul. 16, 2019, Cell Transplantation vol. 21:971-984.

(Continued)

*Primary Examiner* — John D Ulm

(74) *Attorney, Agent, or Firm* — Patterson + Sheridan, LLP

(57) ABSTRACT

Embodiments described herein relate to restorative solutions for segmental peripheral nerve (PN) defects using allografted PNs for stimulating PN repair. More specifically, embodiments described herein provide for localized immunosuppression (LIS) surrounding PN allografts as an alternative to systemically suppressing a patient's entire immune system. Methods include localized release of immunosuppressive (ISV) agents are contemplated in one embodiment. Methods also include localized application of immunosuppressive (ISV) regulatory T-cells (Tregs) in other embodiments. Hydrogel carrier materials for delivery of ISV agents and are also described herein.

20 Claims, 6 Drawing Sheets

(56) References Cited

OTHER PUBLICATIONS

MacDonald, Katherine G. et al., "T regulatory cell therapy in transplantation: stability, localization and functional specialization", Aug. 2012, <https://journals.lww.com/co-transplantation/Abstract/2012/08000/T_regulatory_cell_therapy_in_transplantation_.4.aspx>, last visited on Jul. 16, 2019, Co-Transplantation 17 (4):343-348.

Beyer, Marc et al., "Regulatory T cells in cancer", Blood, Aug. 2006, <http://www.bloodjournal.org/content/bloodjournal/108/3/804.full.pdf?sso-checked=true> last visited Jul. 16, 2019, vol. 108 (No. 3):804-811.

Castro-Manrreza, Marta E. et al., "Immunoregulation by Mesenchymal Stem Cells: Biological Aspects and Clinical Applications"., National Center for Biotechnology Information, Apr. 2015, <https://www.ncbi.nlm.nih.gov/pmc/articles/PMC4417567/>, last visited Jul. 16, 2019, Journal of Immunology Research vol. 2015, Art No. 394917, 20 pages.

Marek, Natalia et al., "Coating Human Pancreatic Islets With CD4+CD25highCD127 ? Regulatory T Cells as a Novel Approach for the Local Immunoprotection", Annals of Surgery, Sep. 2011, <http://strategmed.tregs.gumed.edu.pl/wp-content/uploads/2015/01/Marek-N-2011-AnnSurgery.pdf>, last visited Jul. 16, 2019, Annals of Surgery 254(3):512-519.

Sakaguchi, Shimon et al., "Regulatory T cells: how do they suppress immune responses?", The Japanese Society for Immunology, Aug. 2009, <https://watermark.silverchair.com/dxp095.pdf?token=AQECAHi208BE49Ooan9kkhW_Ercy7Dm3ZL_9Cf3qfKAc485ysgAAAkMwggi_BgkqhkiG9w0BBwagggIwMIIC LAIBADCCAiUGCSqGSIb3DQEHATAeBgIghkgBZQMEAS4wE QQMYcjpXmPNQ43q920DAgEQgIIB9gwqh4R2WYH9sxz3QOQ wodVU7WBKB-TKf24LrfWgS-VOXuJ3oYfVIF_N-, vol. 21 (No. 10):1105-1111.

Ghannam, Soufiane et al., "Immunosuppression by mesenchymal stem cells: mechanisms and clinical applications", Stem Cell Research & Therapy, Mar. 2010, <https://www.ncbi.nlm.nih.gov/pmc/articles/PMC2873698/>, last visited Jul. 16, 2019, vol. 2010, 1:2, 7 pages.

Wan, Yisong Y., "Regulatory T cells: immune suppression and beyond", Cell Mol. Immunol., May 2010, <https://www.ncbi.nlm.nih.gov/pmc/articles/PMC2868372/>, last visited Jul. 16, 2019, Cellular and Molecular Immunology (2010) 7:204-210.

LOCALIZED IMMUNOSUPPRESSION OF ALLOGRAFTS FOR PERIPHERAL NERVE REPAIR

CROSS-REFERENCE TO RELATED APPLICATIONS

This application is a continuation of and claims benefit to U.S. patent application Ser. No. 15/457,359, filed Mar. 13, 2017, which claims benefit of U.S. Provisional Patent Application No. 62/307,290, filed Mar. 11, 2016, both of which are hereby incorporated by reference in their entirety.

BACKGROUND

Field

Embodiments of the present disclosure generally relate to methods and materials for peripheral nerve (PN) repair.

Description of the Related Art

Peripheral nerves (PNs) branch extensively through the body and are fundamental for motor control, sensation, and function of organ systems. Conventional treatment for segmental PN defects include direct coaptation of nerve stumps, insertion of a mixed (motor+sensory) PN autograft, autografted sensory nerves, decellularized/processed allografted nerves, and biodegradable conduits.

Conduits and processed (decellularized) allografts are not currently capable of matching the regeneration associated with sensory autografts (typically the sural nerve), which is typically considered the clinical standard for PN regeneration. PN autografts require a secondary surgery with significant associated morbidity. Moreover, PN autografts suffer from a limited supply of correctly sized nerves. Size mismatch leads to formation of neuromas and poor functional regeneration.

Mixed PN autografts stimulate superior nerve regeneration when compared to sensory autografts, however, mixed nerves are not viable autograft options in most clinical cases. Schwann cells that myelinate motor or sensory axons intrinsically differ with one another, as Schwann cells that associate with motor axons differentially express several biomolecules that facilitate axon growth and guiding motor axons to correctly reinnervate motor branch points. As a result, sensory grafts that lack motor-associated Schwann cells are not an optimal solution for repair of mixed PNs. An additional limitation of autografts and bioengineered strategies is that neither option is ideally suited to bridge segmental nerve defects of complex nerve structures, such as defects that encompass branch points.

PN allografts are contemplated as a solution to the limitations of PN autografts. While harvesting and screening of donor tissue has advanced considerably, continual systemic immunosuppresion (SIS) carries substantial risks of opportunistic infections, renal damage, and post-transplant lymphoproliferative disorders. Patient compliance can also be problematic as many patients fail to adhere to their immunosuppressive treatment regimens, resulting in graft failure. These risks outweigh the potential benefit of allografted PNs.

Hundreds of thousands of injuries to PNs occur each year that require surgical intervention. Thus, what is needed in the art are improved methods and materials for peripheral nerve repair.

SUMMARY

In one embodiment, a method of peripheral nerve grafting is provided. The method includes delivering a calcineurin inhibitor to a peripheral nerve allograft site in vivo, delivering a glucocorticoid to the peripheral nerve allograft site in vivo, and delivering an antibody to the peripheral nerve allograft site in vivo. The calcineurin inhibitor, the glucocorticoid, and the antibody are delivered locally to the peripheral nerve allograft site in vivo by a pharmaceutically acceptable carrier.

In another embodiment, a method of peripheral nerve grafting is provided. The method includes locally delivering in vivo to a peripheral nerve allograft site via a photopolymerizable hydrogel, one or more immunosuppressive agents selected from the group consisting of a calcineurin inhibitor, a glucocorticoid, and an antibody.

In yet another embodiment, a biomaterial carrier for delivery of immunosuppressive agents is provided. The material includes a photopolymerizable poly(ethylene glycol) bulk hydrogel material, a first poly(lactic-co-glycolic acid) material nanoparticle disposed in the bulk hydrogel material, the first poly(lactic-co-glycolic acid) material nanoparticle comprising a calcineurin inhibitor, a second poly(lactic-co-glycolic acid) material nanoparticle disposed in the bulk hydrogel material, the second poly(lactic-co-glycolic acid) material nanoparticle comprising a glucocorticoid, and a third poly(lactic-co-glycolic acid) material nanoparticle disposed in the bulk hydrogel material, the third poly(lactic-co-glycolic acid) material nanoparticle comprising antibodies.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1A:
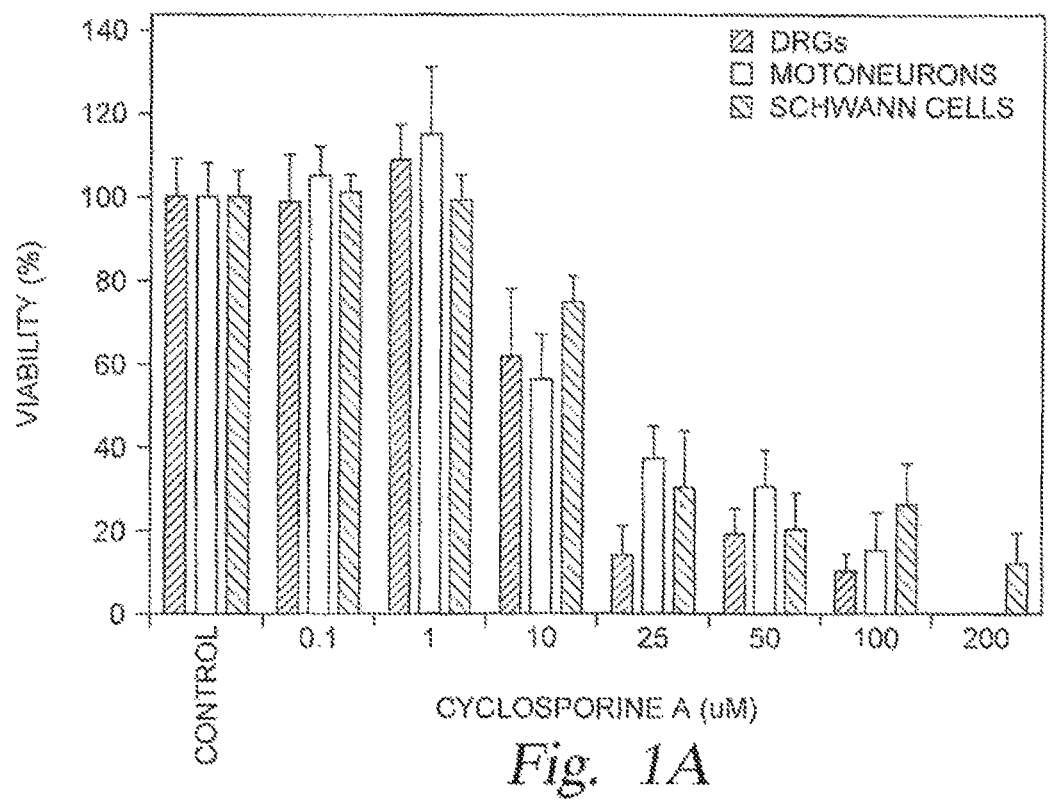
FIG. 1A illustrates data regarding the toxicity of cyclosporine A (CsA) to primary dorsal root ganglion sensory neurons (DRGs), motor neurons, and Schwann cells according to embodiments described herein.

Embodiments described herein relate to restorative solutions for segmental peripheral nerve (PN) defects using allografted PNs for stimulating PN repair. More specifically, embodiments described herein provide for localized immunosuppression (LIS) surrounding PN allografts as an alternative to systemically suppressing a patient's entire immune system. Methods include localized release of immunosuppressive (ISV) agents are contemplated in one embodiment. Methods also include localized application of immunosuppressive (ISV) regulatory T-cells (Tregs) in other embodiments. Hydrogel carrier materials for delivery of ISV agents and are also described herein.

Localized immunosuppression is defined herein as delivering immunosuppressive agents in the local environment of a peripheral nerve allograft, thereby eliminating or minimizing the utilization of immunosuppressive agents for systemic delivery following implantation of a peripheral nerve allograft to treat a segmental peripheral nerve defect. Immunosuppressive agents are defined herein as therapeutics with biological activity that suppresses the activation and activity of the immune response against allografted peripheral nerve tissue. Immunosuppressive agents include, but are not limited to, small molecule therapeutics, peptides, proteins, glycans, antibodies and cells.

Methods for delivery of said immunosuppressive agents, encompassing all methods for localized delivery of said immunosuppressive agents to the allograft site, include, but are not limited to, microfluidics and catheterization to deliver agents from internal or external devices to the allograft site, implantation of biocompatible biomaterial carriers in local proximity to the allogrograft, such as, biomaterials consisting of poly(ethylene glycol), poly(lactic acid), poly(lactic-co-glycolic) acid, collagen, and fibrin, among others, that release said agents to the allograft, and other pharmaceutical formulations for localized release.

Allografts are contemplated as a solution to the limitations of PN autografts. Within an allografted PN there are the same support cells and structure as are found in autografted PNs, but allografted nerves can be mixed. Allografted mixed PNs stimulate regeneration of injured PNs to the same extent or superior to mixed autologous nerves. Allografts additionally have the potential to bridge complex segmental nerve defects, such as branch points, as PN allografts may be harvested from a donor to the exact region corresponding to the segmental defect in the recipient. Such nerves can be correctly sized for length and diameter to avoid neuromas.

Allografted PNs are distinct relative to other tissues with respect to immunosuppression (ISN). The degree of recovery promoted by allografted PNs is believed to be equally effective when systemic immunosuppression (SIS) is stopped after the axons have regenerated when compared to continuous SIS.

Schwann cells are both the major antigenic components of allografted PNs and the cell type providing much of the regenerative stimulus. It is contemplated that once the motor and sensory axons cross through the allografted nerve segment to innervate distal targets, the allogeneic Schwann cells either lower their immunogenic profile upon myelination of host axons or that the allogeneic Schwann cells can be targeted by the immune system without long lasting effects on the regenerated nerve.

It is contemplated that by delaying the immune response to the graft, a sufficient delay in the immune response to a PN allograft can be achieved through local application of immunosuppressants instead of systemic application of immunosuppressants. Localized immunosuppression minimizes the risks associated with ISV therapy. For example, local administration of ISV agents leaves the immune response in the rest of the body largely intact. In addition, lower doses of ISV agents administered locally are much less likely to cause kidney damage as comparatively negligible amounts of ISV agents enter the circulatory system.

Still further, localized and temporary immunosuppression is much less likely to contribute to causing lymphoproliferative disorders. Moreover, patient compliance is not a concern if sufficient administration of immunosuppressive agents for the entire recovery period can be applied during initial surgery. It is believed that allografted PNs may improve functional recovery of segmental PN defects because allografted PNs take advantage of temporary immunosuppression, thereby facilitating clinical adoption for PN repair.

It is also contemplated that localized immunosuppression through localized delivery of immunosuppressive agents will remove or minimize utilization of systemic immunosuppression. For example, instead of daily systemic immunosuppression for peripheral nerve allografts during the initial regeneration period, systemic immunosuppression may be delivered on a less frequent basis, thus, improving the quality of care for the patient and improving prospects for patient compliance.

Acute rejection of nerve transplants is primarily mediated by T-cells. Following transplantation of a nerve segment, antigen presenting cells (APCs) of donor or host origin activate host T-cells by displaying alloantigens via major-histocompatibility complex (MHC) molecules to the αβT-cell receptors (TCRs) of T-cells, with CD4+ and CD8+ T-cells the primary effector T-cells. Activation of T-cells by APCs can occur locally to the site of the allograft, however, activation of T-cells is more robust when the APCs migrate to a lymphatic center. Chronic rejection occurring over months to years involves B-cell activation and progressive infiltration of macrophages into the graft vasculature. As PN allografts utilize the benefits of temporary immunosuppression, which may span weeks to months, it is contemplated that PN allografts are not subject to functional impairment associated with the timeline of chronic rejection. Accordingly, embodiments described herein provide for a reduced response of effector T-cells to enable PN allograft acceptance via localized immunosuppression.

Calcineurin inhibitors (CNIs), such as cyclosporine A (CsA) and tacrolimus (examples of immunosuppressive agents), are contemplated for utilization with PN allograft transplantation. CNIs prevent activation of T-cells by binding to immunophilins and increasing their affinity for calcineurin, thereby inhibiting calcineurin activation of NFAT and NFkB transcription. CNIs are also associated with preventing or reducing production of IL-2 and other immune activating cytokines. Interestingly, both tacrolimus and CsA have neuroprotective effects even in the absence of transplanted cells or tissues.

Prednisolone is the active form of the glucocorticoid prednisone, a pro-drug metabolized into prednisolone, which may be utilized as another example of an immunosuppressive agent and may be utilized for PN allografts according to embodiments described herein. Prednisolone may also be utilized in combination with CNIs for PN allografts in other embodiments. Anti T-cell antibodies, mammalian or otherwise, are also contemplated for localized immunosuppression to protect against the eventuality that APCs will migrate to lymphatic centers and activate effector T-cells outside of the zone of localized immunosuppression. Suitable anti T-cell antibodies for utilization in human subjects include, but are not limited to ATGAM, visilizumab, alemtuzumab, basiliximab, and daclizumab, among others.

Binding of anti T-cell antibodies (such as R73 and MRC Ox-8, rat model described infra) to αβTCRs on CD4+ and CD8+ cells mitigates the risk of APC migration. Moreover, anti T-cell antibodies may substantially prevent or reduce TCR-MHC binding and target T-cells for depletion via opsonization for phagocytosis or lysis due to complement activation against the T-cell. Tacrolimus, prednisolone, and anti T-cell antibodies referred to herein are also contemplated within the definition of immunosuppressive agents.

Tregs are a sub-population of CD4+ cells and suppress activated effector T-cells through a variety of mechanisms linked to Treg FoxP3 expression. Generally, Tregs function of APCs and effector T-cell populations and proliferate in response to IL-2 and down-regulate the adaptive immune response of effector T-cells. Tregs also attenuate graft versus host disease and a number of other autoimmune disorders. Accordingly, embodiments described herein contemplate local application of Tregs for suppression of an acquired immune response to PN allografted tissue. In addition, mesenchymal stromal cells (MSCs) are also an immunosuppressive cell type contemplated for localized delivery suppress the immune response to allografted PNs as MSCs attenuate many autoimmune diseases and deactivate effector T-cells.

Figure 1B:
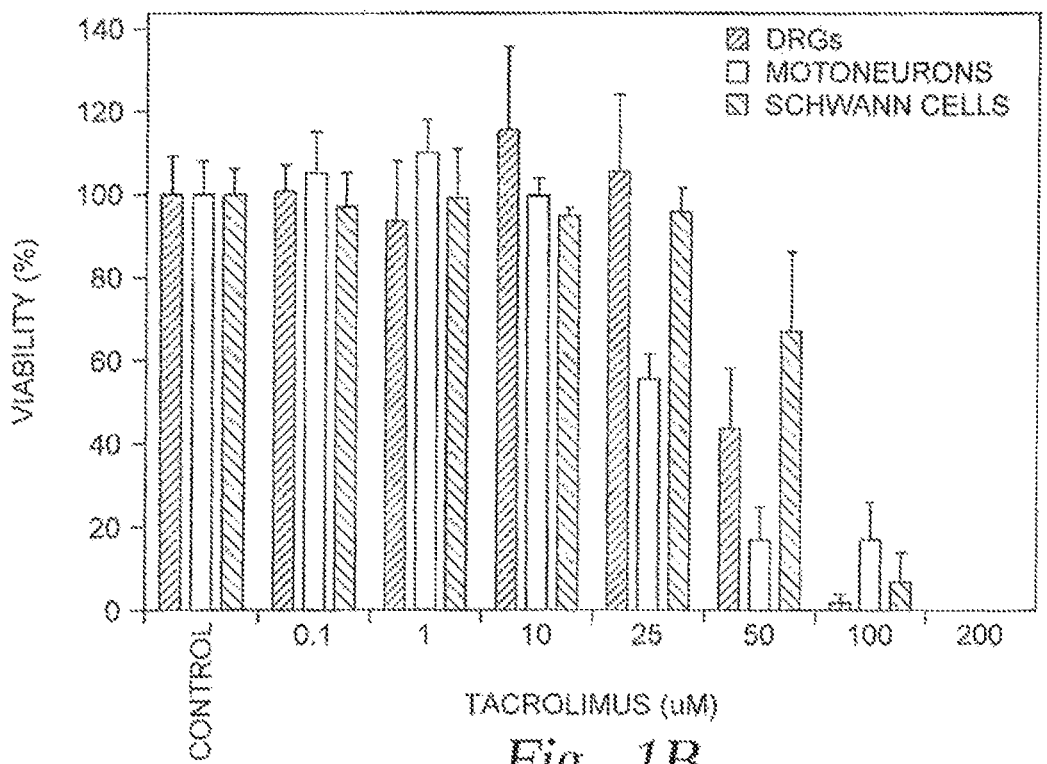
FIG. 1B illustrates data regarding the toxicity of tacrolimus to DRGs, motor neurons, and Schwann cells according to embodiments described herein.
Figure 1C:
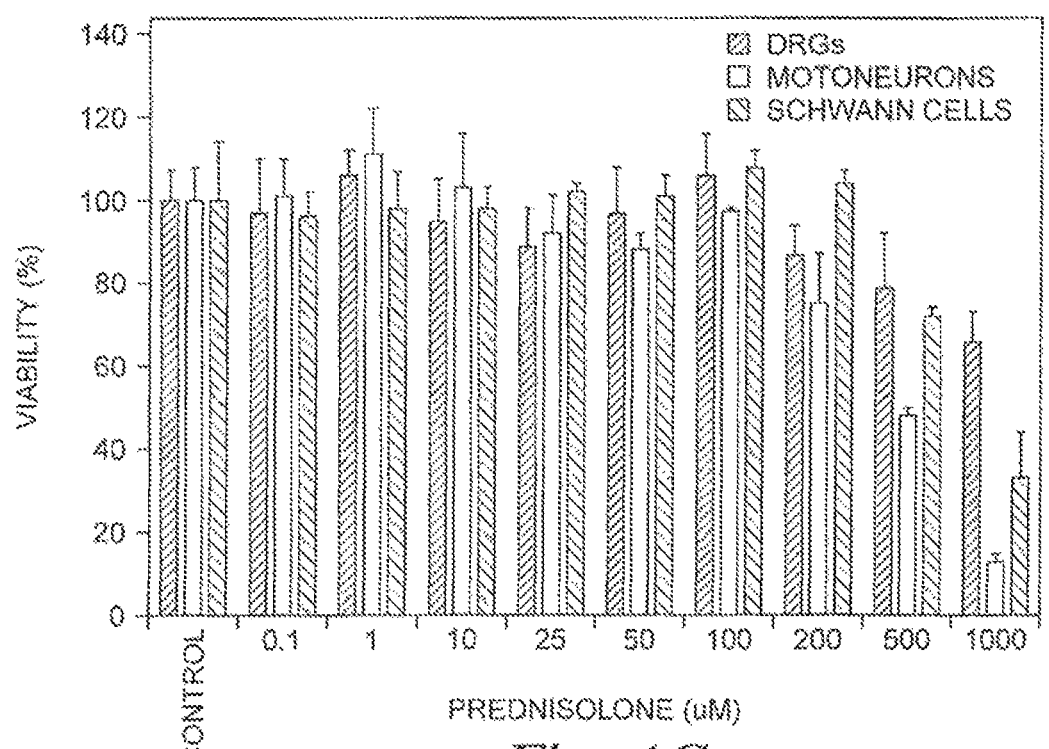
FIG. 1C illustrates data regarding the toxicity of prednisolone to DRGs, motor neurons, and Schwann cells according to embodiments described herein.

It is contemplated that delivery of immunosuppressive agents function within a favorable therapeutic window. PNs are comprised of three major nervous system cell types, motor neurons, sensory neurons, and Schwann cells. FIG. 1A illustrates data regarding the toxicity of CsA to dorsal root ganglion sensory neurons (DRGs), motor neurons, and Schwann cells. FIG. 1B illustrates data regarding the toxicity of tacrolimus to DRGs, motor neurons, and Schwann cells. FIG. 1C illustrates data regarding the toxicity of prednisolone to DRGs, motor neurons, and Schwann cells.

Cells (DRGs, motor neurons, and Schwann cells) were cultured for 72 hours in various concentration of the immunosuppressive drugs and viability was evaluated using the Alamar blue viability assay. ISV's were diluted into media using a maximum of 1% dimethylsulfoxide (DMSO). The results indicated in FIG. 1A indicate that CsA is tolerated by the cells at doses up to about 1 μM, which is significantly greater than the effective dose of CsA (about 25 μM) for inhibiting activation and proliferation of the immune cells.

Figure 2A:
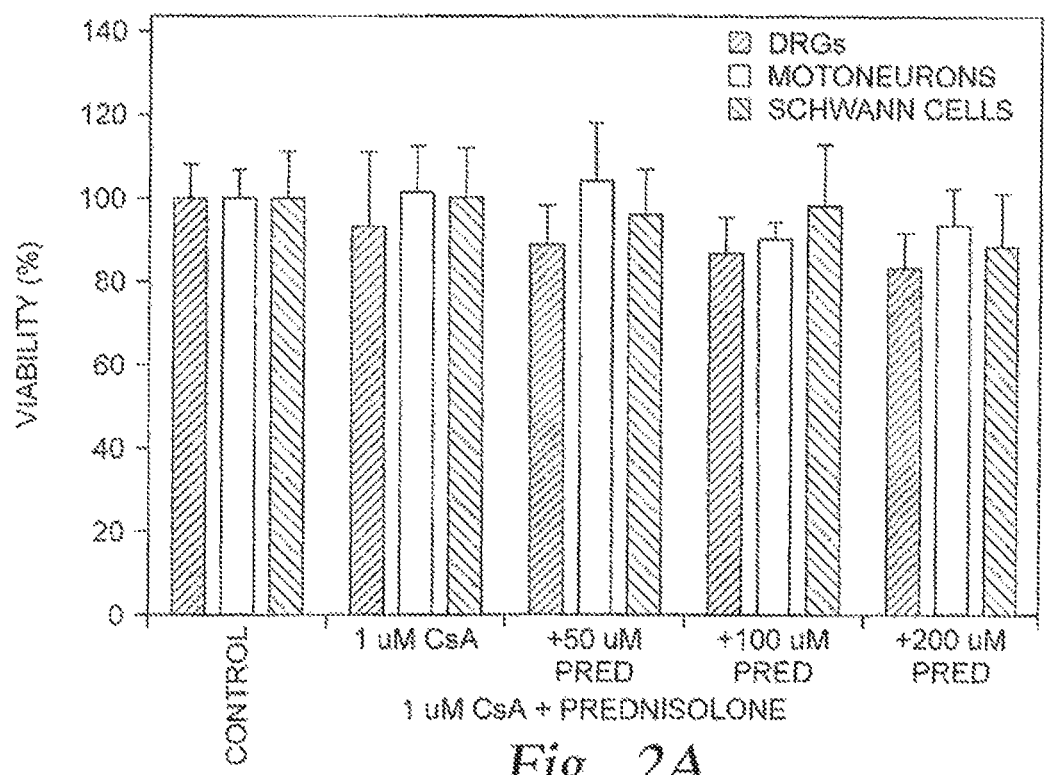
FIG. 2A illustrates data regarding the viability of DRGs, motor neurons, and Schwann cells cultured in about 1 µM CsA with differing concentrations of prednisolone according to embodiments described herein.
Figure 2B:
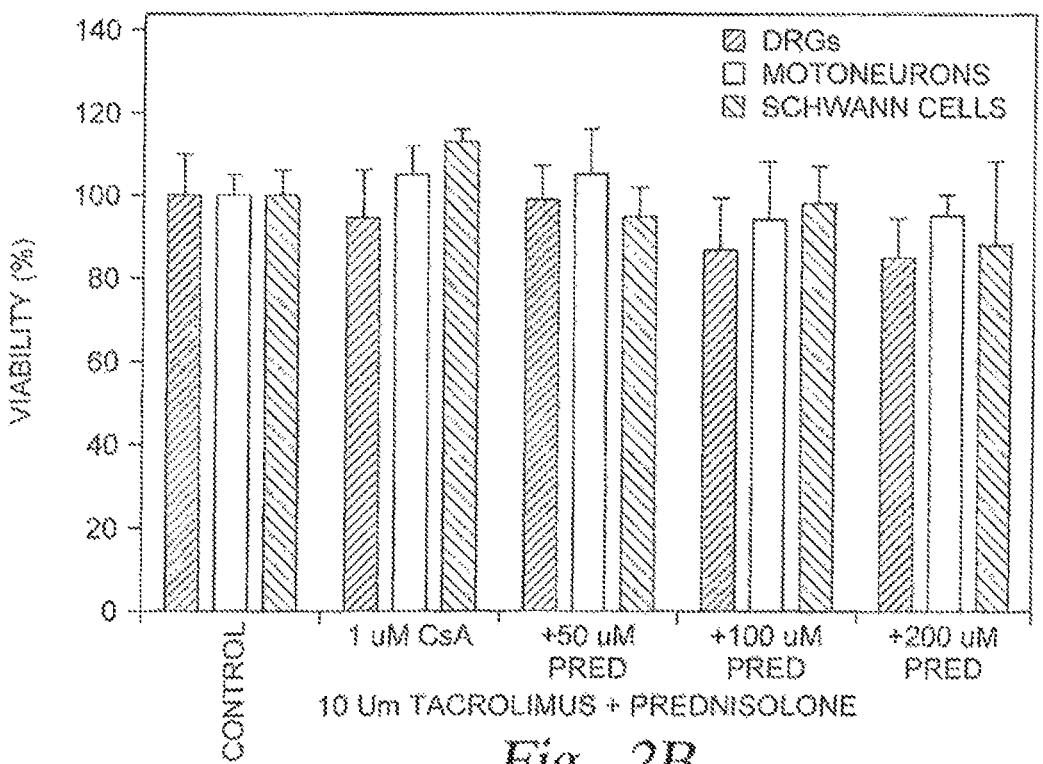
FIG. 2B illustrates data regarding the viability of DRGs, motor neurons, and Schwann cells cultured in about 10 µM tracrolimus with differing concentrations of prednisolone according to embodiments described herein.

The results indicated in FIG. 1B indicate that tacrolimus is tolerated by the cells at doses up to between about 10 μM and about 25 μM, which is greater than the effective dose of tacrolimus (between about 50-100 μM) for inhibiting activation and proliferation of immune cells. The results indicated in FIG. 1C indicate that prednisolone is tolerated by the cells at doses up to about 200 μM, which is greater than the effective dose of prednisolone (greater than about 240 μM) for inhibiting activation and proliferation of immune cells FIG. 2A illustrates data regarding the viability of DRGs, motor neurons, and Schwann cells cultured in about 1 μM CsA with differing concentrations of prednisolone. FIG. 2B illustrates data regarding the viability of DRGs, motor neurons, and Schwann cells cultured in about 10 μM tracrolimus with differing concentrations of prednisolone. In other words, the cells were exposed to the highest tolerated doses of CsA and tacrolimus with increasing doses of prednisolone and no toxicity was observed. Thus, it is contemplated that CNIs may be utilized in combinations with prednisolone for localized immunosuppression.

Experimental Methods

Biological material from Sprague Dawley (GFP- and GFP+) and Lewis rats, without any pathological conditions, were utilized to determine the PN allograft methods and materials described herein. Lewis rats were obtained from Charles River Laboratories (Wilmington, Mass.) and Sprague Dawley rats were obtained from Rat Resource and Research Center (Columbia, Mo.). Alzet osmotic pumps (model 1004), commercially available from DURECT Corporation, Cupertino, Calif., were utilized for delivery of immunosuppressive agents to PN allografts.

For animal experiments, Sprague Dawley (SD) PN allografts were implanted within Lewis recipients, which are respectively $RT1^l$ and $RT1^b$ for major histocompatibility complex (MHC). Donor sciatic nerves are harvested from SD rats under isofluorane anesthesia and connective and other non-nerve tissue was removed. Under sterile "no touch" techniques, the left sciatic nerve of recipient Lewis rats was exposed and a segment of the host nerve was removed that corresponds to a length of the allograft being inserted, spanning approximately 2 mm distal for the length of the allografted segment to be inserted. 9-0 sutures are used to insert the SD allograft PN.

After suturing the allograft PN into place, osmotic pumps were implanted subcutaneously approximately 2 cm lateral to the surgical cavity. A polyethylene catheter extends from the pump into the tissue cavity, where it is sutured to the suture line that closes the musculature, with approximately 0.75 cm of the catheter remaining within the cavity to release ISV agents. The osmotic pump released 0.11 μl/hr of solution for 28-38 days. The positive control group of daily systemic immunosuppression received intraperotineal (IP) injections of 1 mg/kg tacrolimus the day before surgery and every day thereafter. LIS and vehicle control (70% DMSO 30% PBS) received IP injections of tacrolimus the day before and the day of surgery.

To extrapolate the in vitro effective and tolerated doses of ISV agents to PN and immune cells to a dynamic in vivo environment, the tissue cavity with the sciatic nerve contained 190±22 μl of fluid after suturing the muscles together. This figure was used for the volume in dosage calculations.

Several assumptions were made regarding the flow of interstitial fluid (i.e. turnover within the cavity) in order to calculate drug loading. Based on the osmotic pressure in rat skeletal muscles (−1 to −3 mm Hg) compared to −0.20 mm Hg for the overall body average, brain tissues ranging from +3 to +8 mm Hg and the rate of lymphatic turnover in general, it was postulated that the fluid within the cavity containing the allograft and pump would turnover hourly. On the basis of these measurements, the experiment with parameters outlined in Table 1 was performed.

TABLE 1

| ISV agent | in vitro effective concentration on immune cells | Measures in vitro tolerated concentrations on PN cells | Effective clinical plasma concentration | Targeted concentration within the nerve cavity | Concentrations loaded with implanted osmotic pump |
|---|---|---|---|---|---|
| Tacrolimus | 0.5-1.0 nM | 10-25 μM | 21 nM | 5 μM | 9 mM |
| Prednisolone | 240 nM | 200 μM | 277 nM | 50 μM | 90 mM |
| Anti-TCR antibody | 10 ng/ml | N/A | N/A | 165 ng/ml | 30 μg/ml |

Rats were sacrificed after 1, 4, 6, and 16 weeks following surgery. Longitudinal sections of the nerves were cut and labeled for markers of axons (13-III tubulin—Abcam 1:200) and T-cells (R73—Cederlane Laboratories 1:200). Sections showed that regeneration of axons into the allografts in recipients of LIS was comparable to the positive control of daily SIS. After 1 week, host axons had crossed into the allografts of SIS and LIS recipient animals in line with the organization of the nerve. In contrast, β-III tubulin stains in no ISN and vehicle control animals showed a disorganization of axons and denser accumulation of fibrous tissue at the donor-host boundary as illustrated in FIGS. 3A and 3C.

Figure 3A:
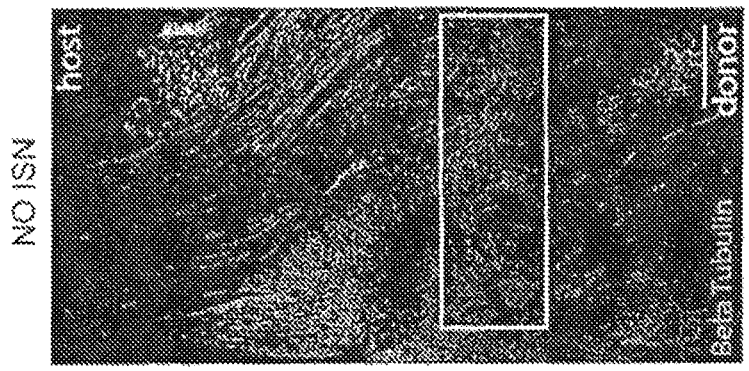
FIG. 3A illustrates a micrograph of a β-III tubulin stained allograft with no immunosuppression according to embodiments described herein.
Figure 3B:
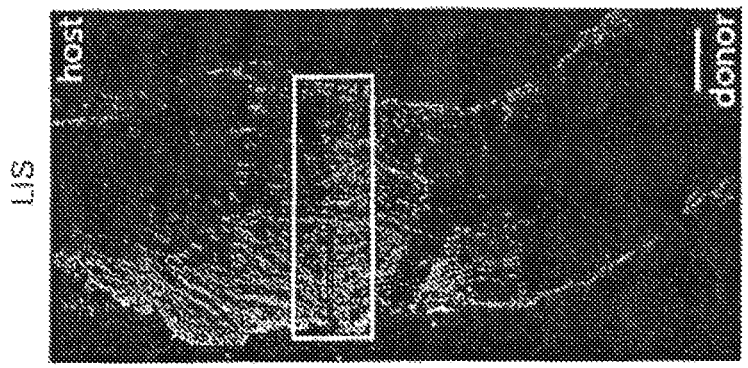
FIG. 3B illustrates a micrograph of a β-III tubulin stained allograft with localized immunosuppression according to embodiments described herein.

After 28 days, allografts with LIS showed axons extending in line from the host nerve into and through the allograft as illustrated in FIG. 3B. The proximal and distal host-donor boundaries, as determined by identifying the proximal and distal suture points, were histologically indistinguishable in LIS recipients, indicating a functional merger of tissues.

Figure 3C:
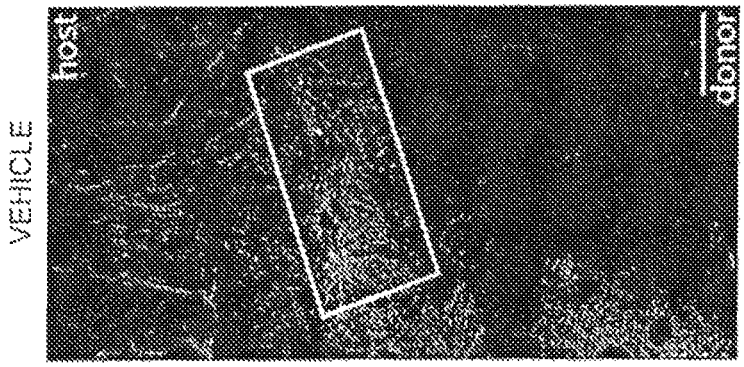
FIG. 3C illustrates a micrograph of a β-III tubulin stained allograft vehicle according to embodiments described herein.

In contrast, negative control groups of vehicle and no ISN showed a lack of axonal crossing into the allograft and robust accumulation of T-cells and apparent scar tissue at the donor-host boundary as illustrated in FIGS. 3A and 3C. Fluorescent densitometry of β-III tubulin was conducted for 10 randomly selected sections within 1 cm² segments, taking the ratio of the signal within the allograft to the proximal host structure, showing a 78±11% reduction in signal intensity of β-III tubulin in the allograft regions of vehicle controls compared to LIS. Accordingly, it is believed that LIS for 28 days is effective at promoting robust regeneration of host axons into allografted PNs, while the negative controls exhibit graft rejection and lack of host axonal entry into the graft which is indicative of long-term graft failure.

Figure 4A:
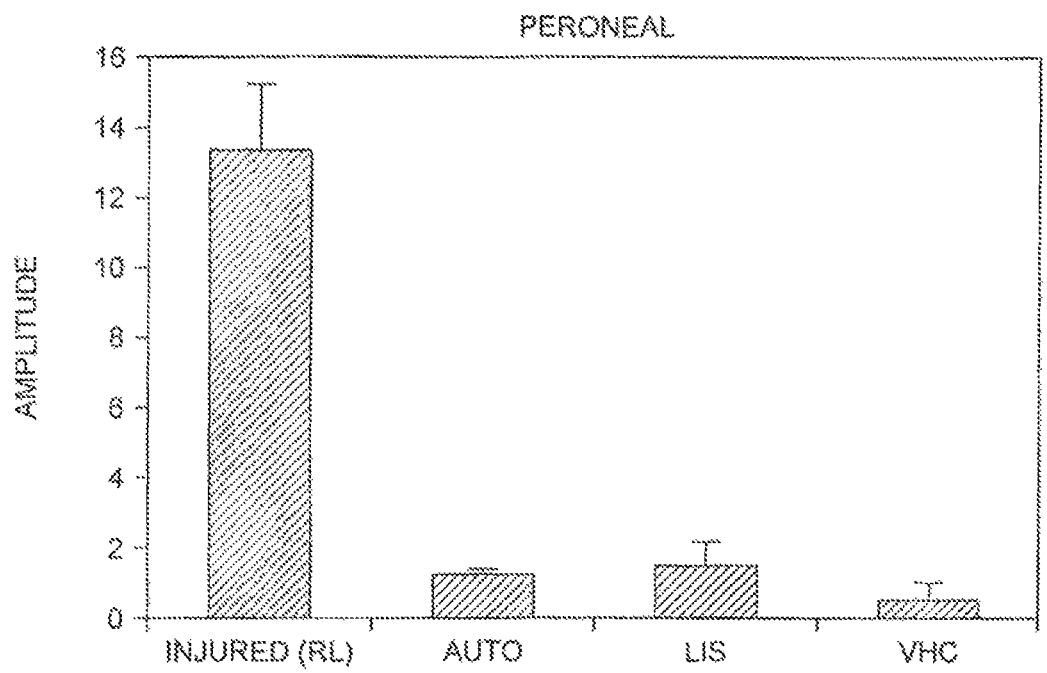
FIG. 4A illustrates compound muscle action potential data of the peroneal branch of the sciatic nerve after PN allograft repair according to embodiments described herein.
Figure 4B:
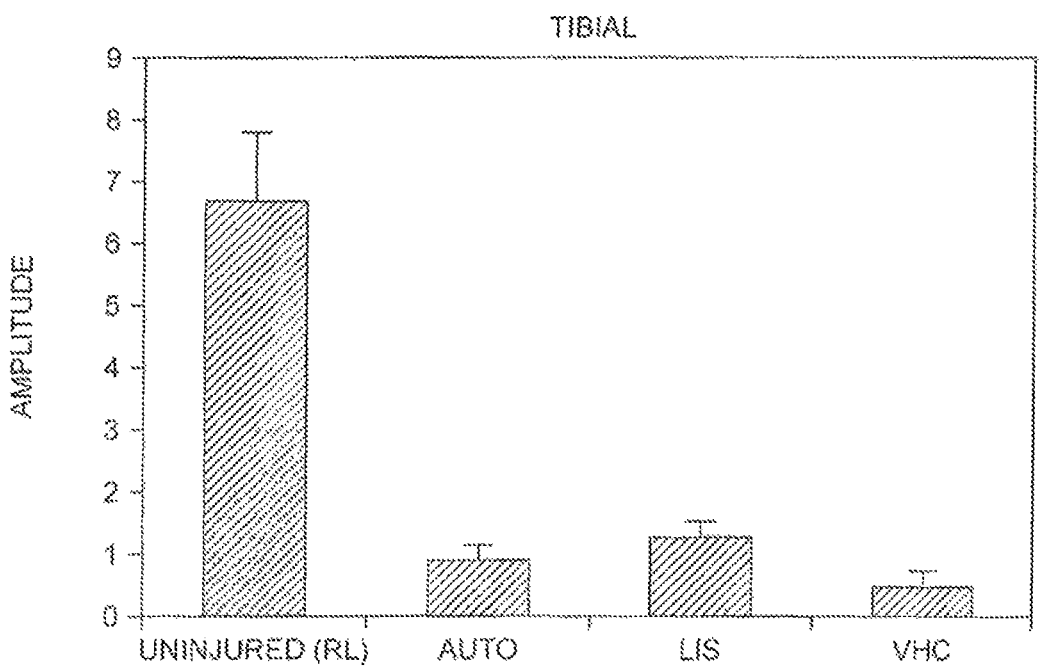
FIG. 4B illustrates compound muscle action potential data of the tibial branch of the sciatic nerve after PN allograft repair according to embodiments described herein.

FIG. 4A illustrates compound muscle action potential (CMAP) data of the peroneal branch of the sciatic nerve after PN allograft repair in the rat experiment described above. FIG. 4B illustrates compound muscle action potential data of the tibial branch of the sciatic nerve after PN allograft repair. CMAPs (electrophysiological measurements) were obtained at the dorsal and planta foot muscles, which are the most distal reinnervation targets of the peroneal and tibial branches of the sciatic nerve. CMAP amplitude measures the strength of nerve signal conduction and corresponds to the number of conducting axons of the regenerated nerve that reached the muscles.

FIG. 4A data, which is based on CMAP tests of the peroneal branch of the sciatic nerve 16 weeks post PN allograft, indicates that PN allografts utilizing localized immunosuppression were at least equivalent to autologous grafts and better than the vehicle. FIG. 4B data, which is based on CMAP tests of the tibial branch of the sciatic nerve 16 weeks post PN allograft, indicates that PN allografts utilizing localized immunosuppression were at least equivalent to autologous grafts and better than the vehicle. Accordingly, it can be seen that localized immunosuppression utilized with a PN allograft provides for desirable PN regeneration without the risks of systemic immunosuppression.

Materials for Isv Agent Delivery

Embodiments described herein provide for materials for ISV agent delivery in a biological system. Materials described herein are contemplated to enable ISV agent delivery for an amount of time greater than one month, such as 2 months or greater. Further, the materials described herein provide an encapsulant that delivers Tregs to the PN allograft. The materials are contemplated to enable controlled release profiles of ISV agents, Tregs cell antibodies, and cells via characteristics of the material composition. A degradation motif, a macromolecular structure, a macromere mass fraction, and a particle size distribution are controllable to enable continual and controlled release of the ISV agents, Tregs cell antibodies, and cells. Moreover, the materials described herein exhibit desirable mechanical flexibility and strain moduli for in vivo application, biodegradability, and bioresorbability, thus, providing additional benefits for a wide range of nerve repair application with reduced morbidity risks.

Microfluidic co-emulsification of biomaterials, ISV, Tregs cell antibodies, and cells enables fabrication of layered particles and confers versatility for application in PN allograft systems with localized immunosuppression. Hydrophobic small molecule therapeutics are formulated into surface-eroding, poly(lactic-co-glycolic acid) (PLGA) polymeric nano-particles, which are subsequently doped into bulk-eroding hydrogel micro-particles composed of photopolymerizable poly(ethylene glycol) (PEG) diacrylate (PEG-DA) or poly(ethylene glycol) norbornene (PEG-NB). In one embodiment, the hydrogel is photopolymerizable, however, it is contemplated that other polymerization techniques may be utilized in accordance with the embodiments described herein. The disclosure of Methods of Generating Microparticles and Porous Hydrogels Using Microfluidics in U.S. patent application Ser. No. 15/335,184 is hereby incorporated by reference in its entirety.

Figure 5A:
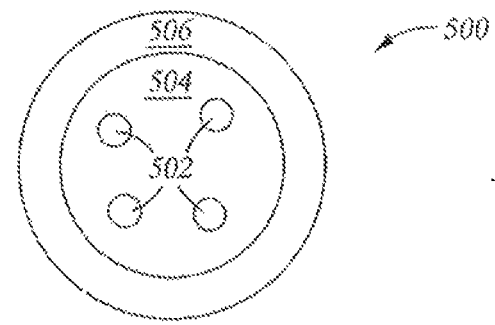
FIG. 5A illustrates a therapeutic delivery vehicle according to embodiments described herein.

FIG. 5A illustrates a delivery vehicle 500 for ISV agent and Tregs cell antibody release. The delivery vehicle 500 is fabricated in a manner to enable time delayed and/or continuous release of the ISV agents and/or Tregs cell antibodies. The delivery vehicle 500 includes a plurality of nanoparticles 502, a first material layer 504, and a second material layer 506. The nanoparticles 502 are interdispersed within the first material layer 504 and the first material layer 504 is encapsulated within the second material layer 506.

In one embodiment, ISV agents, such as CsA, tacrolimus, and/or prednisolone, are dispersed within and supported by the nanoparticles 502. In another embodiment, Tregs cell antibodies are dispersed within the nanoparticles 502. In one embodiment, the nanoparticles 502 comprise PLGA, however it is contemplated that other surface eroding materials suitable for utilization in a biological system may be advantageously utilized according to the embodiments described herein.

The first material layer 504 has the nanoparticles 502 disposed therein and in one embodiment, the first material layer 504 comprises an enzymatically degrading PEG material. The second material layer 506 encapsulates the first material layer 504. In one embodiment, the second material layer 506 comprises a hydrolytically degrading PEG material. The enzymatically degrading PEG material and the hydrolytically degrading PEG material have different degradation rates in one embodiment. For example, the hydrolytically degrading PEG material may have a degradation rate greater than a degradation rate of the enzymatically degrading PEG material. In other words, the hydrolytically degrading PEG material decomposes faster than the enzymatically degrading PEG material. In another example, the hydrolytically degrading PEG material may have a degradation rate less than a degradation rate of the enzymatically degrading PEG material. In other words, the hydrolytically degrading PEG material decomposes slower than the enzymatically degrading PEG material. In another embodiment, the enzymatically degrading PEG material and the hydrolytically degrading PEG material have similar degradation rates.

Figure 5B:
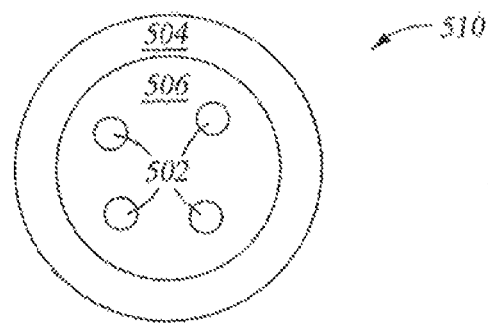
FIG. 5B illustrates a therapeutic delivery vehicle according to embodiments described herein.

FIG. 5B illustrates a delivery vehicle 510 for ISV agent and Tregs cell antibody release. Similar to the delivery vehicle 500, the delivery vehicle 510 is fabricated in a manner to enable time delayed and/or continuous release of the ISV agents and/or Tregs cell antibodies. The delivery vehicle 510 includes the plurality of nanoparticles 502, the first material layer 504, and the second material layer 506. The nanoparticles 502 are interdispersed within the second material layer 506 and the second material layer 506 is encapsulated within the first material layer 504.

Figure 5C:
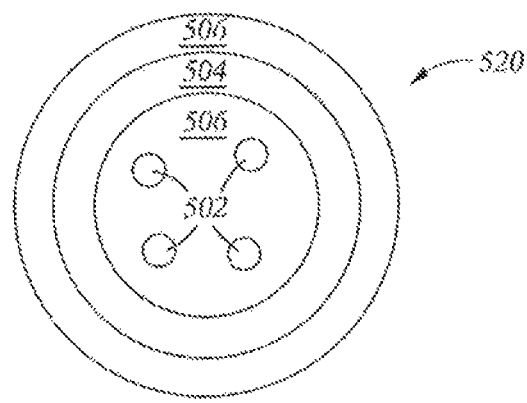
FIG. 5C illustrates a therapeutic delivery vehicle according to embodiments described herein.

FIG. 5C illustrates a delivery vehicle 520 for ISV agent and Tregs cell antibody release. Similar to the delivery vehicles 500, 510, the delivery vehicle 520 is fabricated in a manner to enable time delayed and/or continuous release of the ISV agents and/or Tregs cell antibodies. The delivery vehicle 520 includes the plurality of nanoparticles 502, the first material layer 504, and a plurality of second material layers 506. The nanoparticles 502 are interdispersed within the second material layer 506 and the second material layer 506 is encapsulated within the first material layer 504. An additional second material layer 506 encapsulates the first material layer 504. In another embodiment, the nanoparticles 502 may be interdispersed within the first material layer 504 and the first material layer 504 may be encapsulated with the second material layer 506. An additional first material layer 504 may encapsulate the second material layer 506.

Figure 5D:
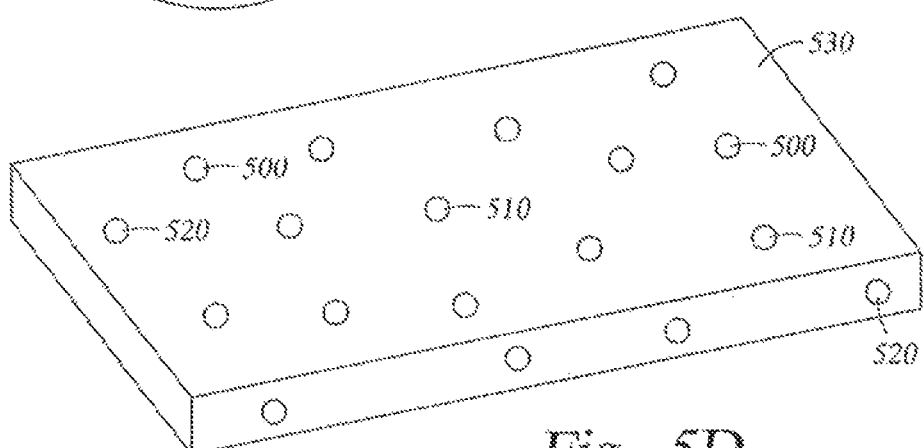
FIG. 5D illustrates a hydrogel system according to embodiments described herein.

FIG. 5D illustrates a bulk hydrogel material 530 having a plurality of delivery vehicles disposed therein. In one embodiment, the hydrogel material 530 is a PEG material. In another embodiment, the hydrogel material 530 is a PLGA material. Various different types of delivery vehicles, such as the delivery vehicles 500, 510, and 520 may be dispersed throughout the hydrogel material 530 to application to a PN allograft. In one embodiment, the hydrogel material 530 is photopolymerizable. In operation, after performing a PN allograft, the hydrogel material having drug loaded delivery vehicles disposed therein is injected locally to the nerve cavity around the PN allograft. The hydrogel material is then photopolymerized to improve the structural integrity of the material within the nerve cavity around the PN allograft.

As described above, small molecules can be retained in and released from hydrogel architectures that are more suited to viably maintain encapsulated materials. By utilizing various combinations of enzymatically and hydrolytically degrading PEG materials, in combination with the PLGA material of the nanoparticles, various ISV agents and Tregs cell antibodies may be released in a time controllable manner via an in situ polymerizable hydrogel material.

PEG hydrogels provide for synthetically modifying the backbone and crosslink architecture, and therefore, the mechanical and diffusive properties of the hydrogel network. The mechanism and kinetics of degradation affect network properties over time as crosslinks break in response to environmental stimuli. Examples of degradation motifs include hydrolysis, thermoresponsive de-gelation, optical cleavage of crosslinks, and enzymatic degradation. Combining the degradation motifs and blending functional PEG copolymers generate hydrogels with complex porosity and mesh size distributions over time and space. Accordingly, any pharmacological compounds loaded within the hydrogel network will be released when crosslink degradation sufficiently opens the network for diffusion.

Enzymatically degradable particles degrade in response to MMPs secreted by the allograft or native axon. Accordingly, successively longer lag times before PLGA particles are exposed and begin to degrade can be achieved. Modulating the particle size distribution provides smooth and tunable release profiles. Release profiles of ISV agents, Tregs cell antibodies, and cells are a function of particle structure, size, and encapsulating phase composition. For example, the encapsulation of ISV agents loaded PLGA nanoparticles within enzymatically degradable PEG hydrogel particles can be protected by encapsulating the PLGA nanoparticles within a hydrolytically degradable PEG-PLA hydrogel. The PEG-PLA matrix is believed prevent the diffusion of MMPs to the core, thus preventing erosion of the enzymatically degradable encapsulant until the programmed degradation of the PEG-PLA shell is complete.

The injectable delivery system further includes microfluidically-generated microscale particles suspended within a continuous PEG-based hydrogel-forming solution that will be polymerized in situ at the PN allograft site. Immunosuppressive agents or cells may be enclosed within either compartment. Both microscale hydrogel droplets and continuous carrier phase materials are to be crosslinked with a variety of hydrolytically and enzymatically degradable motifs to provide control over the spatial distribution of degradation rate of ISV agents, Tregs cell antibodies, and other cells.

In summation, methods and material for localized immunosuppression of PN allografts are described herein. Various immunosuppressive agents may be utilized alone or in combination with one another to facilitate immunosuppression locally to a PN allograft. Materials which provide for delivery of the immunosuppressive agents enable time released and locally controllable delivery which can be utilized to facilitate reinnervation post PN allograft without the risks commonly associated with systemic immunosuppression.

While the foregoing is directed to embodiments of the present disclosure, other and further embodiments of the disclosure may be devised without departing from the basic scope thereof, and the scope thereof is determined by the claims that follow.

What is claimed is:

1. A method of peripheral nerve grafting, comprising:
delivering one or both of T-regs and mesenchymal stromal cells to a peripheral nerve allograft site via a pharmaceutically acceptable carrier.

2. The method of claim 1, wherein the delivering one or both of T-regs and mesenchymal stromal cells to a peripheral nerve allograft site is performed in vivo.

3. The method of claim 1, wherein the delivering one or both of T-regs and mesenchymal stromal cells to the peripheral nerve allograft site is performed locally.

4. The method of claim 1, wherein the pharmaceutically acceptable carrier is a hydrogel material.

5. The method of claim 4, wherein the one or both of T-regs and mesenchymal stromal cells are dispersed within the hydrogel material.

6. The method of claim 4, wherein the hydrogel material is selected from the group consisting of poly(ethylene glycol), poly(ethylene glycol) diactylate, poly(ethylene glycol) norbornene, and poly(lactic-co-glycolic acid).

7. The method of claim 1, further comprising:
photopolymerizing the pharmaceutically acceptable carrier after delivery to the peripheral nerve allograft site.

8. The method of claim 4, further comprising:
photopolymerizing the hydrogel material after delivery to the peripheral nerve allograft site.

9. A method of peripheral nerve grafting, comprising:
delivering a calcineurin inhibitor to a peripheral nerve allograft site in vivo;
delivering a glucocorticoid to the peripheral nerve allograft site in vivo; and
delivering one or both of Tregs and mesenchymal stromal cells to the peripheral nerve allograft site in vivo, wherein the calcineurin inhibitor, the glucocorticoid, and the one or both of the Tregs and the mesenchymal stromal cells are delivered locally to the peripheral nerve allograft site by a pharmaceutically acceptable carrier.

10. The method of claim 9, wherein the calcineurin inhibitor is cyclosporine A or tacrolimus.

11. The method of claim 9, wherein the glucocorticoid is prednisolone.

12. The method of claim 9, wherein the pharmaceutically acceptable carrier is a hydrogel material.

13. The method of claim 12, wherein the hydrogel material is photopolymerizable and the hydrogel material is photopolymerized after delivery to the peripheral nerve allograft site.

14. The method of claim 9, further comprising:
encapsulating one or both of the calcineurin inhibitor and the glucocorticoid in a first poly(lactic-co-glycolic acid) material.

15. The method of claim 14, further comprising:
encapsulating the first poly(lactic-co-glycolic acid) material in a second poly(lactic-co-glycolic acid) material.

16. The method of claim 15, wherein the first poly(lactic-co-glycolic acid) material is enzymatically degradable and the second poly(lactic-co-glycolic acid) material is hydrolytically degradable.

17. A method of peripheral nerve grafting, comprising:
locally delivering to a peripheral nerve allograft site via a hydrogel material, an immunosuppressive agent comprising a calcineurin inhibitor, a glucocorticoid, Tregs, and mesenchymal stromal cells.

18. The method of claim 17, wherein the calcineurin inhibitor is cyclosporine A or tacrolimus.

19. The method of claim 17, wherein the glucocorticoid is prednisolone.

20. The method of claim 17, further comprising:
photopolymerizing the hydrogel material.

* * * * *